United States Patent
Jones et al.

(10) Patent No.: US 7,012,145 B2
(45) Date of Patent: Mar. 14, 2006

(54) METHOD

(75) Inventors: Andrew Jones, Boston, MA (US); Jonathan Moseley, Bristol (GB); Ian Patel, Bristol (GB); Evan Snape, Bristol (GB); Maureen Young, Edinburgh (GB)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 10/502,191

(22) PCT Filed: Jan. 23, 2003

(86) PCT No.: PCT/SE03/00114

§ 371 (c)(1), (2), (4) Date: Dec. 22, 2004

(87) PCT Pub. No.: WO03/062203

PCT Pub. Date: Jul. 31, 2003

(65) Prior Publication Data

US 2005/0080104 A1 Apr. 14, 2005

(30) Foreign Application Priority Data

Jan. 24, 2002 (SE) .................................. 0200205

(51) Int. Cl.
C07D 215/12 (2006.01)
C07D 215/14 (2006.01)
A61K 31/47 (2006.01)

(52) U.S. Cl. ...................... 546/167; 546/158; 514/311; 514/314; 514/297

(58) Field of Classification Search ................ 514/311, 514/297, 314; 546/167, 168
See application file for complete search history.

(56) References Cited

U.S. PATENT DOCUMENTS 5,455,253 A 10/1995 Ohnmacht, Jr. et al.
5,622,964 A 4/1997 Ohnmacht, Jr. et al.

FOREIGN PATENT DOCUMENTS

WO    WO 9528388 A1    10/1995
WO    WO 02/10134 A1 *    2/2002

OTHER PUBLICATIONS

Ashworth, Tetrahedron Leters, vol. 43, pp 4931-4933, 2002.*

* cited by examiner

*Primary Examiner*—D. Margaret Seaman
(74) *Attorney, Agent, or Firm*—Kenneth F. Mitchell; Paul K. Legaard

(57) ABSTRACT

Process for preparing 3-[(4S)-5-oxo-2-(trifluoromethyl)-1,4,5,6,7,8-hexahydroquinolin-4-yl]benzonitrile, pharmaceutical compositions containing the compound and methods of treatment using the same.

10 Claims, No Drawings

METHOD

This application is a 371 of PCT/SE03/00114, filed Jan. 23, 2003.

FIELD OF THE INVENTION

This invention relates to the synthesis of compounds useful as smooth muscle relaxants in mammals and particularly to the synthesis of compounds useful for treating overactive bladder in mammals and particularly in humans.

BACKGROUND

Inappropriate smooth muscle activation is believed to be involved in many conditions and diseases including, hypertension, asthma, peripheral vascular disease, right heart failure, congestive heart failure, angina, ischemic heart disease, cerebrovascular disease, renal colic, disorders associated with kidney stones, irritable bowel syndrome, male-pattern baldness, premature labor, impotence, peptic ulcers, overactive bladder and urinary incontinence.

Processes for the synthesis of 1,4-dihydropyridines have been described in U.S. Pat. Nos. 5,455,253 and 5,622,964 and in PCT publication WO 95/28388.

DESCRIPTION OF THE INVENTION

We have discovered a new process by which 4-(3-cyanophenyl)-5-oxo-2-(trifluoromethyl)-1,4,5,6,7,8-hexahydroquinoline-3-carboxylic acid may be prepared with improved yield and greater purity. Advantageously, the process is suitable for implementation on an industrial scale.

In the invented process, an ester of 4,4,4-trifluoro-3-oxobutanoate is reacted with 1,3-cyclohexanedione and 3-cyanobenzaldehyde to form an ester of 4-(3-cyanophenyl)-2-hydroxy-5-oxo-2-(trifluoromethyl)-1,2,3,4,5,6,7,8-octahydroquinoline-3-carboxylate. The 4-(3-cyanophenyl)-2-hydroxy-5-oxo-2-(trifluoromethyl)-1,2,3,4,5,6,7,8-octahydroquinoline-3-carboxylate ester is dehydrated to form a urethane, which is an ester of 4-(3-cyanophenyl)-5-oxo-2-(trifluoromethyl)-1,4,5,6,7,8-hexahydroquinoline-3-carboxylate. The urethane is de-esterified to form 4-(3-cyanophenyl)-5-oxo-2-(trifluoromethyl)-1,4,5,6,7,8-hexahydroquinoline-3-carboxylic acid.

A variety of esters have been found to be suitable for use in the invented process.

One aspect of the invention is a process to prepare the racemic acid from esters by cleavage with Wilkinson's catalyst.

Another aspect of the invention is a process to prepare the racemic acid from isoprenol or geraniol esters by acid cleavage without the need for Wilkinson's catalyst Yet another aspect of the invention is a process to prepare the racemic acid from para-nitrobenzyl esters by cleavage with Pd(0)/$H_2$.

A particular aspect of the invention is a method of making 4-(3-cyanophenyl)-5-oxo-2-(trifluoromethyl)-1,4,5,6,7,8-hexahydroquinoline-3-carboxylic acid, comprising: a) reacting an ester of 4,4,4-trifluoro-3-oxobutanoate with 1,3-cyclohexanedione and 3-cyanobenzaldehyde to form an ester of 4-(3-cyanophenyl)-2-hydroxy-5-oxo-2-(trifluoromethyl)-1,2,3,4,5,6,7,8-octahydroquinoline-3-carboxylate; b) dehydrating said ester of 4-(3-cyanophenyl)-2-hydroxy-5-oxo-2-(trifluoromethyl)-1,2,3,4,5,6,7,8-octahydroquinoline-3-carboxylate to form an ester of 4-(3-cyanophenyl)-5-oxo-2-(trifluoromethyl)-1,4,5,6,7,8-hexahydroquinoline-3-carboxylate, and c) de-esterifying said ester of 4-(3-cyanophenyl)-5-oxo-2-(trifluoromethyl)-1,4,5,6,7,8-hexahydroquinoline-3-carboxylate to form 4-(3-cyanophenyl)-5-oxo-2-(trifluoromethyl)-1,4,5,6,7,8-hexahydroquinoline-3-carboxylic acid. In this aspect of the invention in particular step a) is performed in ethanol in the presence of ammonium acetate; step b) is achieved with p-toluenesulfonic acid in n-butyl acetate, and step c) is achieved with chlorotris(triphenylphosphine)rhodium.

Another particular aspect of the invention is a method of making 3-[(4S)-5-oxo-2-(trifluoromethyl)-1,4,5,6,7,8-hexahydroquinolin-4-yl]benzonitrile, comprising: a) reacting an ester of 4,4,4-trifluoro-3-oxobutanoate with 1,3-cyclohexanedione and 3-cyanobenzaldehyde to form an ester of 4-(3-cyanophenyl)-2-hydroxy-5-oxo-2-(trifluoromethyl)-1,2,3,4,5,6,7,8-octahydroquinoline-3-carboxylate; b) dehydrating said ester of 4-(3-cyanophenyl)-2-hydroxy-5-oxo-2-(trifluoromethyl)-1,2,3,4,5,6,7,8-octahydroquinoline-3-carboxylate to form an ester of 4-(3-cyanophenyl)-5-oxo-2-(trifluoromethyl)-1,4,5,6,7,8-hexahydroquinoline-3-carboxylate; c) de-esterifying said ester of 4-(3-cyanophenyl)-5-oxo-2-(trifluoromethyl)-1,4,5,6,7,8-hexahydroquinoline-3-carboxylate to form 4-(3-cyanophenyl)-5-oxo-2-(trifluoromethyl)-1,4,5,6,7,8-hexahydroquinoline-3-carboxylic acid; d) resolving racemic 4-(3-cyanophenyl)-5-oxo-2-(trifluoromethyl)-1,4,5,6,7,8-hexahydroquinoline-3-carboxylic acid by co-crystallization of said 4-(3-cyanophenyl)-5-oxo-2-(trifluoromethyl)-1,4,5,6,7,8-hexahydroquinoline-3-carboxylic acid with (1S)-1-phenylethyl-1-amine; e) recovering (1S)-1-phenylethan-1-aminium (4S)-4-(3-cyanophenyl)-5-oxo-2-(trifluoromethyl)-1,4,5,6,7,8-hexahydroquinoline-3-carboxylate; f) decarboxylating said (4S)-4-(3-cyanophenyl)-5-oxo-2-(trifluoromethyl)-1,4,5,6,7,8-hexahydroquinoline-3-carboxylate, and g) recovering 3-[(4S)-5-oxo-2-(trifluoromethyl)-1,4,5,6,7,8-hexahydroquinolin-4-yl]benzonitrile. In this aspect of the invention in particular step e) is achieved by crystallization from ethanol; step f) is achieved by decarboxylation with 1-methylpyrrolidone, and step g) is achieved by crystallization from acetonitrile.

Yet another particular aspect of the invention is 3-[(4S)-5-oxo-2-(trifluoromethyl)-1,4,5,6,7,8-hexahydroquinolin-4-yl]benzonitrile made as described herein or a pharmaceutically-acceptable salt thereof.

Still another particular aspect of the invention is the use of a compound made as described herein for preparation of a medicament.

Yet a further particular aspect of the invention is a pharmaceutical composition comprising a compound made as described herein together with at least one pharmaceutically-acceptable excipient or diluent.

4-(3-cyanophenyl)-5-oxo-2-(trifluoromethyl)-1,4,5,6,7,8-hexahydroquinoline-3-carboxylic acid is a potent opener of K-ATP channels of smooth muscle tissues. Such channels are found in human bladder smooth muscle (i.e., detrusor). Functional selectivity studies indicate little or no interaction with other ion channels or receptors. The compound initiates a robust cellular hyperpolarization that causes detrusor muscle relaxation. The antispasmodic activity of the compound is dose-dependent and is competitively antagonized by the K-ATP channel blocker, glibenclamide.

Accordingly, another aspect of the invention is a method of treating a disease or condition that results from inappropriate smooth muscle activation comprising administering a therapeutically effective amount of a compound made as described herein.

A particular aspect of the invention is a method for treating a disease or condition selected from hypertension, asthma, peripheral vascular disease, right heart failure, congestive heart failure, angina, ischemic heart disease, cerebrovascular disease, renal colic, disorders associated with kidney stones, irritable bowel syndrome, male-pattern baldness, premature labor, impotence, peptic ulcers, overactive bladder or urinary incontinence that result from or involve inappropriate smooth muscle activation another aspect of the invention is a method for treating a disease or condition that results from or involves inappropriate smooth muscle activation with a compound prepared by the described process.

Yet a more particular method of the invention is a method for treating overactive bladder or urinary incontinence with a compound made as described herein or a pharmaceutically-acceptable salt thereof.

The process of the invention is illustrated in Scheme I wherein Step A is performed by refluxing in a lower alcohol solvent in the presence of ammonium acetate; Step B is performed at a temperature and in a solvent with an acid suitable for effecting the dehydration of a substituted octahydroquinoline, and Step C is performed in the presence of a catalyst and a suitable nucleophile Scheme I:

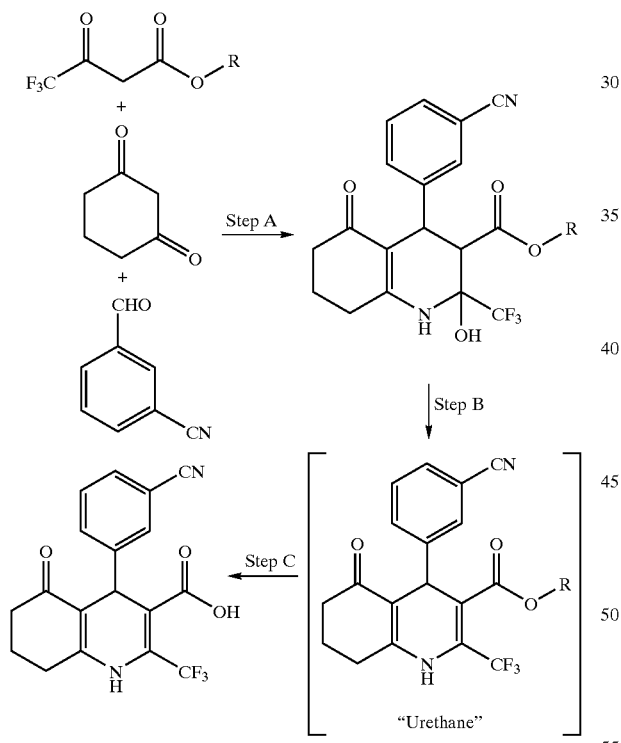

Suitable solvents for the performance of Step A ate methanol, ethanol or propanol. Suitable solvents for performing Step B are toluene or butyl acetate heated to an elevated temperature in the presence of para-toluene sulfonic acid, acetic acid, methane sulfonic acid or trifluoroacetic acid. A suitable catalyst for performing Step C is palladium(0) on carbon 10 under atmospheric pressure hydrogen at ambient temperature, or in methanol with ammonium form ate under reflux; or, Wilkinson's catalyst in water, ethanol and acetic acid. R is as defined in Scheme 3 in Example 2, below.

Particular conditions and solvents for carrying out Steps A, B and C are described in the Examples.

Resolution of Racemate:

Racemic 4-(3-cyanophenyl)-5-oxo-2-(trifluoromethyl)-1,4,5,6,7,8-hexahydroquinoline-3-carboxylic acid is resolved by co-crystallizing 4-(3-cyanophenyl)-5-oxo-2-(trifluoromethyl)-1,4,5,6,7,8-hexahydroquinoline-3-carboxylic acid with (1S)-1-phenylethyl-1-amine. (1S)-1-phenylethan-1-aminium (4S)-4-(3-cyanophenyl)-5-oxo-2-(trifluoromethyl)-1,4,5,6,7,8-hexahydroquinoline-3-carboxylate is crystallized from a suitable solvent and the (4S) compound is decarboxylated and recovered by recrystallization.

The process for resolution of the racemate and preparation of 3-[(4S)-5-oxo-2-(trifluoromethyl)-1,4,5,6,7,8-hexahydroquinolin-4-yl]benzonitrile is illustrated in Scheme II.

Scheme II:

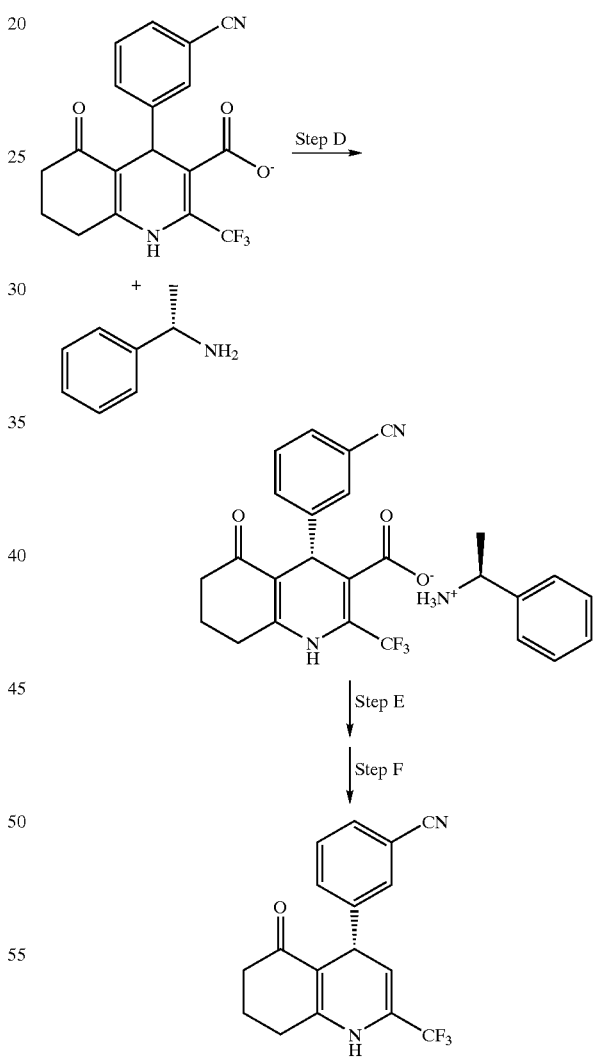

Suitable solvents for performing the crystallization of Step D of Scheme II are substantially anhydrous solvents. Step E is performed with a solvent suitable to permit a temperature of 95° C. to be achieved. Step F is performed in a solvent suitable to afford crystallization of the product.

Particular solvents for Step D are absolute ethanol. IMS and iso-propanol/toluene mixtures; a solvent suitable for carrying out Step E is 1-methylpyrrolidone, and in Step F the product can be crystallized from acetonitrile or methanol.

Particular conditions and solvents for carrying out Steps D, E and F are described in the Examples.

Other solvents suitable for carrying out each of the reactions described herein will be apparent to those of skill in the art upon an appreciation of the processes described herein.

Abbreviations Used Herein:

| | |
|---|---|
| NH$_4$OAc: | Ammonium acetate |
| EtOH: | Ethanol |
| pTSA: | p-Toluenesulfonic acid |
| BuOAc: | Butyl acetate |
| IMS | Industrial Methylated Spirits |
| i-PrOH: | iso-Propanol |
| MTBE: | Methyl tert-butyl ether |
| NMP: | 1-Methylpyrrolidone |
| MeCN: | Acetonitrile |
| RhCl(PPh$_3$)$_3$ | Chlorotris(triphenylphosphine)rhodium, (Wilkinson's catalyst) |

Experimental Procedures:

EXAMPLE 1

Preparation of Allyl 4-(3-cyanophenyl)-2-hydroxy-5-oxo-2-trifluoromethyl)-1,2,3,4,5,6,7,3-octahydro-quinoline-3-carboxylate A slurry of 3-cyanobenzaldehyde and ammonium acetate was prepared in ethanol at ambient temperature. To the slurry a solution of 1,3-cyclohexanedione in ethanol was added at a constant rate. Allyl 4,4,4-trifluoro-3-oxobutanoate was added at a constant rate, followed by ammonium acetate and ethanol. The reaction was heated to reflux and maintained at reflux. Excess ethanol was removed by distillation under vacuum and water was added. The mixture was then cooled to ambient temperature, filtered, washed with water and MTBE. The title compound was obtained by drying in vacuo to constant weight.

Preparation of 4-(3-cyanophenyl)-5-oxo-2-(trifluoromethyl)-1,4,5,6,7,8-hexahydroquinoline-3-carboxylic acid Allyl 4-(3-cyanophenyl)-2-hydroxy-5-oxo-2-(trifluoromethyl)-1,2,3,4,5,6,7,8-octahydroquinoline-3-carboxylate was stirred in n-butyl acetate with pTSA at 125° C. The reaction was cooled, filtered under reduced pressure, the organic phase recovered and washed with water to remove pTSA. Water, ethanol and acetic acid were added to the solution of allyl 4-(3-cyanophenyl)-5-oxo-2-(trifluoromethyl)-1,4,5,6,7,8-hexahydroquinoline-3-carboxylate. Wilkinson's catalyst (chlorotris(triphenylphosphine) rhodium) was added to the batch and the mixture degassed with sub-surface nitrogen for 30 minutes. The mixture was heated to 70–75° C. for 3–5 hours under a constant flow of nitrogen and then cooled to 20° C. to form the racemic acid The title compound was extracted into 2 M NaOH and the aqueous phase was washed with butyl acetate. The aqueous phase is recharged to the vessel and methanol was added followed by 2 M HCl added slowly. The mixture was stirred and the product collected by filtration under reduced pressure, washed with water, dried by suction and dried in vacuo to constant weight.

Preparation of 3-[(4S)-5-oxo-2-(trifluoromethyl)-1,4,5,6,7,8-hexahydroquinolin-4-yl]benzonitrile 4-(3-Cyanophenyl)-5-oxo-2-(trifluoromethyl)-1,4,5,6,7,8-hexahydroquinoline-3-carboxylic acid was co-crystallized with (1S)-1-phenylethyl-1-amine from absolute ethanol or to form (1S)-1-phenylethan-1-aminium (4S)-4-(3-cyanophenyl)-5-oxo-2-(trifluoromethyl)-1,4,5,6,7,8-hexahydroquinoline-3-carboxylate as shown in Scheme II. The carboxylate was de-carboxylated by treatment with 1-methylpyrrolidone at 95° C. and the title compound recrystallized from acetonitrile.

EXAMPLE 2

Preparation of Esters of 4,4,4-trifluoro-3-oxobutanoate

Esters of 4,4,4-trifluoro-3-oxobutanoate suitable for use in the process described in Scheme I were prepared as shown in Scheme 3.

Scheme 3:

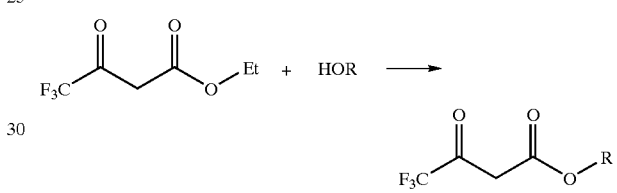

wherein HOR is selected from allyl alcohol, isoprenol, geraniol, cinnamyl alcohol or para-nitrobenzylalcohol.

To perform the reaction, ethyl 4,4,4-trifluoro-3-oxobutanoate is heated with the appropriate alcohol. Trans-esterification is driven by providing an excess of the alcohol reagent over the ester and by removal of the formed ethanol by distillation.

EXAMPLE 3

Isoprenol and geraniol derived esters prepared essentially as described in Example 2, were dehydrated and the ester cleaved under acidic conditions in the presence of para-toluene sulfonic acid to afford the racemic acid.

Accordingly, another aspect of the invention is a process to prepare the racemic acid from isoprenol or geraniol esters by acid cleavage without the need for Wilkinson's catalyst.

EXAMPLE 4

Cinnamyl ester prepared essentially as described in Example 2 was shown to form a corresponding urethane compound upon dehydration.

EXAMPLE 5

Para-nitrobenzyl ester prepared essentially as described in Example 2 was dehydrated and the ester cleaved by Pd(0)/H$_2$ to afford the racemic acid.

Accordingly, another aspect of the invention is a process to prepare the racemic acid from para-nitrobenzyl esters by cleavage with Pd(0)/H$_2$.

We claim:

1. A method of making 4-(3-cyanophenyl)-5-oxo-2-(trifluoromethyl)-1,4,5,6,7,8-hexahydroquinoline-3-carboxylic acid, comprising:
   a) reacting an ester of 4,4,4-trifluoro-3-oxobutanoate with 1,3-cyclohexanedione and 3-cyanobenzaldehyde to form an ester of 4-(3-cyanophenyl)-2-hydroxy-5-oxo-2-(trifluoromethyl)1,2,3,4,5,6,7,8-octahydroquinoline-3-carboxylate;
   b) dehydrating said ester of 4-(3-cyanophenyl)-2-hydroxy-5-oxo-2-(trifluoromethyl)-1,2,3,4,5,6,7,8-octahydroquinoline-3-carboxylate to form an ester of 4-(3-cyanophenyl)-5-oxo-2-(trifluoromethyl)-1,4,5,6,7,8-hexahydroquinoline-3-carboxylate, and
   c) de-esterifying said ester of 4-(3-cyanophenyl)-5-oxo-2-(trifluoromethyl)-1,4,5,6,7,8-hexahydroquinoline-3-carboxylate to form 4-(3-cyanophenyl)-5-oxo-2-(trifluoromethyl)-1,4,5,6,7,8-hexahydroquinoline-3-carboxylic acid.

2. The method of claim 1, wherein:
   step a) is performed in ethanol in the presence of ammonium acetate;
   step b) is achieved with p-toluenesulfonic acid in n-butyl acetate, and
   step c) is achieved with chlorotris(triphenylphosphine)rhodium.

3. A method of making 3-[(4S)-5-oxo-2-(trifluoromethyl)-1,4,5,6,7,8-hexahydroquinolin-4-yl]benzonitrile, comprising:
   a) reacting an ester of 4,4,4-trifluoro-3-oxobutanoate with 1,3-cyclohexanedione and 3-cyanobenzaldehyde to form an ester of 4-(3-cyanophenyl)-2-hydroxy-5-oxo-2-(trifluoromethyl)-1,2,3,4,5,6,7,8-octahydroquinoline-3-carboxylate;
   b) dehydrating said ester of 4-(3-cyanophenyl)-2-hydroxy-5-oxo-2-(trifluoromethyl)-1,2,3,4,5,6,7,8-octahydroquinoline-3-carboxylate to form an ester of 4-(3-cyanophenyl)-5-oxo-2-(trifluoromethyl)-1,4,5,6,7,8-hexahydroquinoline-3-carboxylate;
   c) de-esterifying said ester of 4-(3-cyanophenyl)-5-oxo-2-(trifluoromethyl)-1,4,5,6,7,8-hexahydroquinoline-3-carboxylate to form 4-(3-cyanophenyl)-5-oxo-2-(trifluoromethyl)-1,4,5,6,7,8-hexahydroquinoline-3-carboxylic acid;
   d) resolving racemic 4-(3-cyanophenyl)-5-oxo-2-(trifluoromethyl)-1,4,5,6,7,8-hexahydroquinoline-3-carboxylic acid by co-crystallization of said 4-(3-cyanophenyl)-5-oxo-2-(trifluoromethyl)-1,4,5,6,7,8-hexahydroquinoline-3-carboxylic acid with (1S)-1-phenylethyl-1-amine;
   e) recovering (1S)-1-phenylethan-1-aminium (4S)-4-(3-cyanophenyl)-5-oxo-2-(trifluoromethyl)-1,4,5,6,7,8-hexahydroquinoline-3-carboxylate;
   f) decarboxylating said (4S)-4-(3-cyanophenyl)-5-oxo-2-(trifluoromethyl)-1,4,5,6,7,8-hexahydroquinoline-3-carboxylate, and
   g) recovering 3-[(4S)-5-oxo-2-(trifluoromethyl)-1,4,5,6,7,8-hexahydroquinolin-4-yl]benzonitrile.

4. The method according to claim 3, wherein:
   step e) is achieved by crystallization from ethanol;
   step f) is achieved by decarboxylation with 1-methylpyrrolidone, and
   step g) is achieved by crystallization from acetonitrile.

5. The method of claim 1, wherein step a) is performed in ethanol in the presence of ammonium acetate.

6. The method of claim 1, wherein step b) is achieved with p-toluenesulfonic acid in n-butyl acetate.

7. The method of claim 1, wherein step c) is achieved with chlorotris(triphenylphosphine)rhodium.

8. The method according to claim 3, wherein step e) is achieved by crystallization from ethanol.

9. The method according to claim 3, wherein step f) is achieved by decarboxylation with 1-methylpyrrolidone.

10. The method according to claim 3, wherein step e) is achieved by crystallization from acetonitrile.

* * * * *